(12) United States Patent
Wang et al.

(10) Patent No.: US 10,600,168 B2
(45) Date of Patent: Mar. 24, 2020

(54) METHOD FOR GENERATING 2D SCAN VIDEOKYMOGRAPHIC IMAGES BY USING REAL-TIME OR PRE-STORED ULTRA-HIGH SPEED LARYNGEAL ENDOSCOPY IMAGES, 2D SCAN VIDEOKYMOGRAPHIC IMAGE GENERATION SERVER FOR PERFORMING SAME, AND RECORDING MEDIUM FOR STORING SAME

(71) Applicants: UMEDICAL CO., LTD., Busan (KR); Yong Jin Wang, Busan (KR); Duck Hoon Kang, Gyeongsangnam-do (KR)

(72) Inventors: Yong Jin Wang, Busan (KR); Duck Hoon Kang, Gyeongsangnam-do (KR)

(73) Assignees: UMEDICAL CO., LTD., Busan (KR); Yong Jin Wang, Busan (KR); Duck Hoon Kang, Gyeongsangnam-do (KR)

( * ) Notice: Subject to any disclaimer, the term of this patent is extended or adjusted under 35 U.S.C. 154(b) by 0 days.

(21) Appl. No.: 15/558,288

(22) PCT Filed: Jun. 9, 2016

(86) PCT No.: PCT/KR2016/006108
§ 371 (c)(1),
(2) Date: Sep. 14, 2017

(87) PCT Pub. No.: WO2017/039124
PCT Pub. Date: Mar. 9, 2017

(65) Prior Publication Data
US 2018/0061030 A1    Mar. 1, 2018

(30) Foreign Application Priority Data
Aug. 31, 2015 (KR) .................. 10-2015-0123110

(51) Int. Cl.
*G06T 5/50* (2006.01)
*A61B 1/04* (2006.01)
(Continued)

(52) U.S. Cl.
CPC .............. *G06T 5/50* (2013.01); *A61B 1/0005* (2013.01); *A61B 1/00009* (2013.01);
(Continued)

(58) Field of Classification Search
CPC ........... G06T 5/50; G06T 7/248; G06T 7/215; G06T 7/11; G06T 5/003; G06T 5/20;
(Continued)

(56) References Cited

U.S. PATENT DOCUMENTS 4,910,590 A * 3/1990 Gillies ............... A61B 1/00147
348/65
2003/0206665 A1* 11/2003 Pettigrew ............ G06F 3/04815
382/284

(Continued)

FOREIGN PATENT DOCUMENTS

KR    1999-0079315 A    11/1999
KR    2014-0115526 A    10/2014
(Continued)

OTHER PUBLICATIONS

Strip Kymography of the Glottis, Archives of OtoRhinoLaryngology 1984.*
(Continued)

*Primary Examiner* — Loi H Tran
(74) *Attorney, Agent, or Firm* — Osha Liang LLP (57) ABSTRACT

A method by which a planar scan videokymographic image generation server generates planar scan videokymographic images by using real-time or pre-stored ultra-high speed laryngeal endoscopy images. The method includes the steps of: (a) acquiring monochrome or color ultra-high speed
(Continued)

laryngeal endoscopy images; (b) setting a target region and a unit pixel for generating the 2D scan videokymographic images from the ultra-high speed laryngeal endoscopy images; (c) extracting pixel information of each frame of the ultra-high speed laryngeal endoscopy images according to the unit pixel for the target region; (d) generating frames of the planar scan videokymographic images by combining the extracted pixel information of each frame; and (e) generating a planar scan videokymographic video by combining the frames of the planar scan videokymographic images.

8 Claims, 6 Drawing Sheets

(51) Int. Cl.
| | | |
|---|---|---|
| *A61B 1/00* | (2006.01) | |
| *A61B 1/267* | (2006.01) | |
| *G06T 7/215* | (2017.01) | |
| *G06T 7/11* | (2017.01) | |
| *G06T 7/246* | (2017.01) | |
| *G06T 5/00* | (2006.01) | |
| *G06T 5/20* | (2006.01) | |

(52) U.S. Cl.
CPC ............ *A61B 1/00045* (2013.01); *A61B 1/04* (2013.01); *A61B 1/267* (2013.01); *A61B 1/2673* (2013.01); *G06T 5/003* (2013.01); *G06T 5/20* (2013.01); *G06T 7/11* (2017.01); *G06T 7/215* (2017.01); *G06T 7/248* (2017.01); *G06T 2207/10016* (2013.01); *G06T 2207/10068* (2013.01)

(58) Field of Classification Search
CPC ............ G06T 7/00; G06T 2007/10016; G06T 2007/10068; A61B 1/2673; A61B 1/00009; A61B 1/00045; A61B 1/0005; A61B 1/267; A61B 1/04
USPC .......................................................... 348/65
See application file for complete search history.

(56) References Cited

U.S. PATENT DOCUMENTS

| | | | |
|---|---|---|---|
| 2005/0219376 A1 | 10/2005 | Wittenberg et al. | |
| 2006/0235693 A1* | 10/2006 | Ruderman ........... | A61B 1/2673 704/270 |
| 2009/0263025 A1* | 10/2009 | Li ........................ | G06K 9/346 382/203 |
| 2009/0281390 A1* | 11/2009 | Qiu ...................... | A61B 1/2673 600/199 |
| 2015/0279425 A1* | 10/2015 | Goranson .............. | G11B 27/34 386/230 |
| 2016/0000370 A1 | 1/2016 | Kim et al. | |

FOREIGN PATENT DOCUMENTS

| | | |
|---|---|---|
| WO | 2014/134501 A2 | 9/2014 |
| WO | 2014/148712 A1 | 9/2014 |

OTHER PUBLICATIONS

International Search Report issued in corresponding application No. PCT/KR2016/006108 dated Sep. 21, 2016 (4 pages).
R. R. Casiano, V. Zaveri, and D. S. Lundy, "Efficacy of videostroboscopy in the diagnosis of voice disorders"; Otolaryngology—Head and Neck Surgery; vol. 107, pp. 95-100; 1992 (7 pages).
H. Hirose, "High-speed digital imaging of vocal fold vibration"; Acta Oto-Laryngologica Suppl.; vol. 458, pp. 151-153; 1988 (4 pages).
J. G. Svec and H. K. Schutte, "Kymographic imaging of laryngeal vibrations"; Current Opinion Otolaryngology Head and Neck Surgery; vol. 20, pp. 458-465; 2012 (8 pages).
T. Wittenberg, M. Tigges, P. Mergell, and U. Eysholdt, "Functional Imaging of Vocal Fold Vibration: Digital Multislice High-Speed Kymography"; Journal of Voice; vol. 14, No. 3, pp. 422-442; 2000 (21 pages).
M. W. Sung, K. H. Kim, T. Y. Koh, T. Y. Kwon, J. H. Mo, S. H. Choi, J. S. Lee, K. S. Park, E. J. Kim, and M. Y. Sung, "Videostrobokymography: A New Method for the Quantitative Analysis of Vocal Fold Vibration"; The Laryngoscope; vol. 109, No. 11, pp. 1859-1863; 1999 (5 pages).
V. Gall, "Strip Kymography of the Glottis"; Arch Otorhinolaryngol; vol. 240, No. 3, pp. 287-288; 1984 (2 pages).
Q. Qiu and H. K. Schulte, "Real-time kymographic imaging for visualizing human vocal-fold vibratory function", Review of Scientific Instruments; vol. 78, No. 2, pp. 1-6; 2007 (7 pages).
S. G. Wang, B. J. Lee, J. C. Lee, Y. S. Lim, Y. M. Park, H. J. Park, J. H. Roh, G. R. Jeon, S. B. Kwon, and B. J. Shin, "Development of Two-Dimensional Scanning Videokymography for Analysis of Vocal Fold Vibration"; Korean Society of Laryngology Phoniatrics and Logopedics; vol. 24, No. 2, pp. 107-111; 2013 (5 pages).
Extended European Search Report issued in corresponding European Application No. 16842090.9 dated Mar. 29, 2019 (7 pages).
V. Gall, "Strip Kymography of the Glottis"; Arch Otorhinolaryngol; Archives of Oto-Rhino-Laryngology, vol. 240, pp. 287-293, 1984 (7 pages).

* cited by examiner

METHOD FOR GENERATING 2D SCAN VIDEOKYMOGRAPHIC IMAGES BY USING REAL-TIME OR PRE-STORED ULTRA-HIGH SPEED LARYNGEAL ENDOSCOPY IMAGES, 2D SCAN VIDEOKYMOGRAPHIC IMAGE GENERATION SERVER FOR PERFORMING SAME, AND RECORDING MEDIUM FOR STORING SAME

TECHNICAL FIELD

The present invention relates to a technology for generating two-dimensional scanning videokymography (2D VKG) images using ultra-high speed laryngeal endoscopy images, and more particularly, to a method of generating 2D VKG images by using real-time or pre-stored ultra-high speed laryngeal endoscopy images in which 2D VKG images, which enable analysis of entire regions of vocal-fold mucosae, are generated from ultra-high speed laryngeal endoscopy images and stored or output to a display device, a 2D VKG image generation server for performing the method, and a recording medium for storing the method.

BACKGROUND ART

Generally, the vocal folds of a human body are vocal organs for communication by a language, and a laryngeal mucosa vibrates about 100 to 250 times per second according to respiration. In other words, air inhaled into a lower airway pressurizes vocal folds closed in a sub-glottal area. When the pressure is greater than a resistance of the vocal folds, a mucosal wave propagating from an inferior margin of the vocal folds to a superior margin thereof is generated, and the vocal folds open to start vocalization. When the pressure is lowered, the vocal folds are closed. This is repeated 100 to 250 times per second to produce a voice.

However, in the case of vocal fold nodules, glottic cancer, vocal fold paralysis, and the like, effective energy conversion of the sub-glottal part is impossible and symmetry of mucosal waves is degraded, leading to an abnormal voice.

Therefore, when abnormality of the voice is diagnosed, it is necessary to identify a motion state of the vocal-fold mucosae. To this end, a method of identifying a motion state of vocal-fold mucosae using stroboscope technology has been developed. Currently, a method using laryngeal videostroboscopy for observing rapid motions of 100 to 250 times per second at slow motion using stroboscopic technology is primarily used. However, a laryngeal videostroboscopic image does not actually show vibrations of vocal folds and is an image obtained by combining some frame images among vocal-fold vibration images of several periods captured at about 20 to 30 frames per second into one period to slowly show motions of the vocal folds. Also, a laryngeal videostroboscopic image has a disadvantage in that accurate motions of vocal folds cannot be acquired as an image when it is not possible to continuously vocalize for five or more seconds or vocalization is irregular.

Much research has been conducted to overcome these disadvantages of laryngeal videostroboscopy, and an ultra-high speed digital video system disclosed by Hirose et al. photographs vocal-fold vibrations at 2,000 frames or more per second and is used as a practical diagnosis tool for evaluating vocal-fold vibrations.

Also, methods of generating a videokymography image by post-processing an image acquired from an ultra-high speed camera and analyzing a mucosal motion state by comparing and observing vibrations of both vocal folds have been developed. However, currently developed videokymographic images have problems in that only a kymogram of one line or multiple lines can be obtained and it is not possible to observe a motion state of an entirety of vocal-fold mucosae from the kymogram.

Recently, Wang et al. has devised a system for observing vibrations of an entirety of vocal folds using the principle of laryngeal photokymography of Gall et al., and has developed two-dimensional scanning videokymography (2D VKG) for examining a vibration state of the entirety of the vocal folds in real time. 2D VKG may avoid distortion caused by a motion of a patient and the like and also enable an analysis of a mucosal motion state through comparative observation of entire regions of both vocal folds.

PRIOR ART LITERATURE

Non-Patent Literature (Non-Patent Literature 1) R. R. Casiano, V. Zaveri, and D. S. Lundy, "Efficacy of videostroboscopy in the diagnosis of voice disorders", Otolaryngol. Head. Neck. Surg., vol. 107, pp. 95-100, 1992.

(Non-Patent Literature 2) H. Hirose, "High-speed digital imaging of vocal fold vibration", Acta Otolaryngol. Suppl., vol 458, pp. 151-153, 1988.

(Non-Patent Literature 3) J. G. Svec and H. K. Schutte, "Kymographic imaging of laryngeal vibrations", Current Opinion Otolaryngology Head and Neck Surgery., vol. 20, pp. 458-465, 2012.

(Non-Patent Literature 4) T. Wittenberg, M. Tigges, P. Mergell, and U. Eysholdt, "Functional imaging of vocal fold vibration: digital multislice ultra-high speed kymography", Journal of Voice, vol. 14, no. 3, pp. 422-442, 2000.

(Non-Patent Literature 5) M. W. Sung, K. H. Kim, T. Y. Koh, T. Y. Kwon, J. H. Mo, S. H. Choi, J. S. Lee, K. S. Park, E. J. Kim, and M. Y. Sung, "Videostrobokymography: a new method for the quantitative analysis of vocal fold vibration", Laryngoscope, vol. 109, no. 11, pp. 1859-63, 1999.

(Non-Patent Literature 6) V. Gall, "Strip kymography of the glottis", Arch. Otorhinolaryngol., vol. 240, no. 3, pp. 287-293, 1984.

(Non-Patent Literature 7) Q. Qiu and H. K. Schutte, "Real-time kymographic imaging for visualizing human vocal-fold vibratory function", Rev. Sci. Instrum., vol. 78, no. 2, pp. 1-6, 2007.

(Non-Patent Literature 8) S. G. Wang, B. J. Lee, J. C. Lee, Y. S. Lim, Y. M. Park, H. J. Park, J. H. Roh, G. R. Jeon, S. B. Kwon, and B. J. Shin, "Development of Two-Dimensional Scanning Videokymography for analysis of Vocal Fold Vibration", Korean Soc. Laryngol. Phoniatr. Logop., vol. 24, no. 2, pp. 107-111, 2013.

DISCLOSURE

Technical Problem

In consideration of the problem in that only a kymogram of one line or multiple lines can be obtained from an ultra-high speed laryngeal endoscopy image, the present invention is directed to providing a method of generating two-dimensional scanning videokymography (2D VKG) images in which 2D VKG images are generated from images of an entire laryngeal region transmitted in real time from an ultra-high speed camera or 2D VKG images are generated by post-processing pre-stored ultra-high speed laryngeal endoscopy images and stored or output to a display device.

Technical Solution

One aspect of the present invention provides a method of generating two-dimensional scanning videokymography (2D VKG) images using real-time or pre-stored ultra-high speed laryngeal endoscopy images in a 2D VKG image generation server, the method including (a) acquiring monochromatic or color ultra-high speed laryngeal endoscopy images, (b) setting a target region and a pixel unit for generating 2D VKG images from the ultra-high speed laryngeal endoscopy images; (c) extracting pixel information of each frame of the ultra-high speed laryngeal endoscopy images according to the pixel unit in the target region; (d) generating frames of 2D VKG images by combining the extracted pixel information of each of each frame; and (e) generating a 2D VKG video by combining the frames of the 2D VKG images.

Preferably, step (a) may include receiving the ultra-high speed laryngeal endoscopy images in real time from an ultra-high speed camera connected to the 2D VKG image generation server or loading ultra-high speed laryngeal endoscopy images pre-stored in the 2D VKG image generation server.

Preferably, step (c) may include extracting pixel information of a specific frame among frames of the ultra-high speed laryngeal endoscopy images and then determining a position next to a position from which the pixel information is extracted as a pixel information extraction position in a frame next to the specific frame.

Preferably, step (d) may include setting the extracted pixel information of each frame as pixel information of a corresponding position in a frame of the 2D VKG images according to an extraction position of the extracted pixel information.

Preferably, step (d) may further include correcting brightness, saturation, blurring, sharpness, or rotation of the frames of the generated 2D VKG images.

Preferably, step (e) may further include storing the 2D VKG video or outputting the 2D VKG video to a display device connected to the 2D VKG image generation server.

Preferably, the pixel unit may correspond to a predetermined number of pixel line of the target region or at least one of pixel constituting a pixel line.

Another aspect of the present invention provides a server for generating 2D VKG images, the server including: an acquisition unit configured to acquire monochromatic or color ultra-high speed laryngeal endoscopy images, a setting unit configured to set a target region and a pixel unit for generating 2D VKG images from the ultra-high speed laryngeal endoscopy images, an extraction unit configured to extract pixel information of each frame of the ultra-high speed laryngeal endoscopy images according to the pixel unit in the target region, a frame generation unit configured to generate frames of 2D VKG images by combining the extracted pixel information of each frame, and a video generation unit configured to generate a 2D VKG video by combining the frames of the 2D VKG images.

Preferably, the acquisition unit may receive the ultra-high speed laryngeal endoscopy images in real time from an ultra-high speed camera connected to the server for generating 2D VKG images or load ultra-high speed laryngeal endoscopy images pre-stored in the server for generating 2D VKG images.

Preferably, the extraction unit may extract pixel information of a specific frame among frames of the ultra-high speed laryngeal endoscopy images and then determine a position next to a position from which the pixel information is extracted as a pixel information extraction position in a frame next to the specific frame.

Preferably, the frame generation unit may set the extracted pixel information of each frame as pixel information of a corresponding position in a frame of the 2D VKG images according to an extraction position of the extracted pixel information.

Preferably, the frame generation unit may correct brightness, saturation, blurring, sharpness, or rotation of the frames of the generated 2D VKG images.

Preferably, the video generation unit may store the 2D VKG video or output the 2D VKG video to a display device connected to the server for generating 2D VKG images.

Advantageous Effects

As described above, according to the present invention, it is possible to solve the problem in that only a kymogram of one line or multiple lines can be obtained, and images of an entire laryngeal region can be generated in real time as two-dimensional scanning videokymography (2D VKG) images and stored or output to a display device.

In particular, ultra-high speed laryngeal endoscopy images are converted into 2D VKG images in real time so that the two kinds of images, that is, the ultra-high speed laryngeal endoscopy images and the 2D VKG images, can be output on one screen or to separate display devices and simultaneously subjected to comparative analysis.

Moreover, it is possible to generate a 2D VKG image using one image captured with an ultra-high speed laryngeal endoscopy camera.

MODES OF THE INVENTION

Advantages and features of the present invention and a method of achieving the same should be clearly understood from embodiments described in detail below with reference to the accompanying drawings. However, the present invention is not limited to the embodiments disclosed below and may be implemented in various different forms. The embodiments are provided merely for complete disclosure of the present invention and to fully convey the scope of the invention to those of ordinary skill in the art to which the present invention pertains. The present invention is only defined by the scope of the claims. The same reference numerals refer to the same components throughout this specification. "And/or" includes any and all combinations of one or more of the associated listed items.

Although the terms "first," "second," etc. may be used to describe various elements, components, and/or sections, these elements, components, and/or sections are not limited by these terms. These terms are only used to distinguish one element, component, or section from another element, component, or section. Therefore, a first element, component, or section mentioned below may be termed a second element, component, or section within the technical spirit of the present invention.

Identification symbols (e.g., a, b, c, etc.) of individual steps are used for convenience of description and do not describe a sequence of the steps. The individual steps may be performed in a sequence different from a described sequence unless a specific sequence is clearly described in the context. In other words, the steps may be performed in the described sequence, performed substantially at the same time, or performed in a reverse sequence.

Terminology used herein is only for the purpose of describing embodiments and is not intended to be limiting to the invention. As used herein, a singular form of a word includes a plural form thereof unless clearly indicated otherwise by context. As used herein, "comprise" and/or "comprising" does not preclude the presence or addition of one or more components, steps, operations, and/or elements other than the stated components, steps, operations, and/or elements.

Unless defined otherwise, all terms (including technical and scientific terms) used herein have the same meanings as commonly understood by those of ordinary skill in the technical field to which the present invention pertains. Terms defined in commonly-used dictionaries are not to be interpreted in an idealized or overly formal sense unless explicitly so defined herein.

When it is determined that the detailed description of a known function or configuration obscures the subject matter of the present invention, the detailed description will be omitted. Terms used herein are defined in consideration of the functions in the present invention and may be replaced with other terms according to the intention or practice of a user or an operator. Therefore, the terms should be defined on the basis of the overall content.

Figure 1:
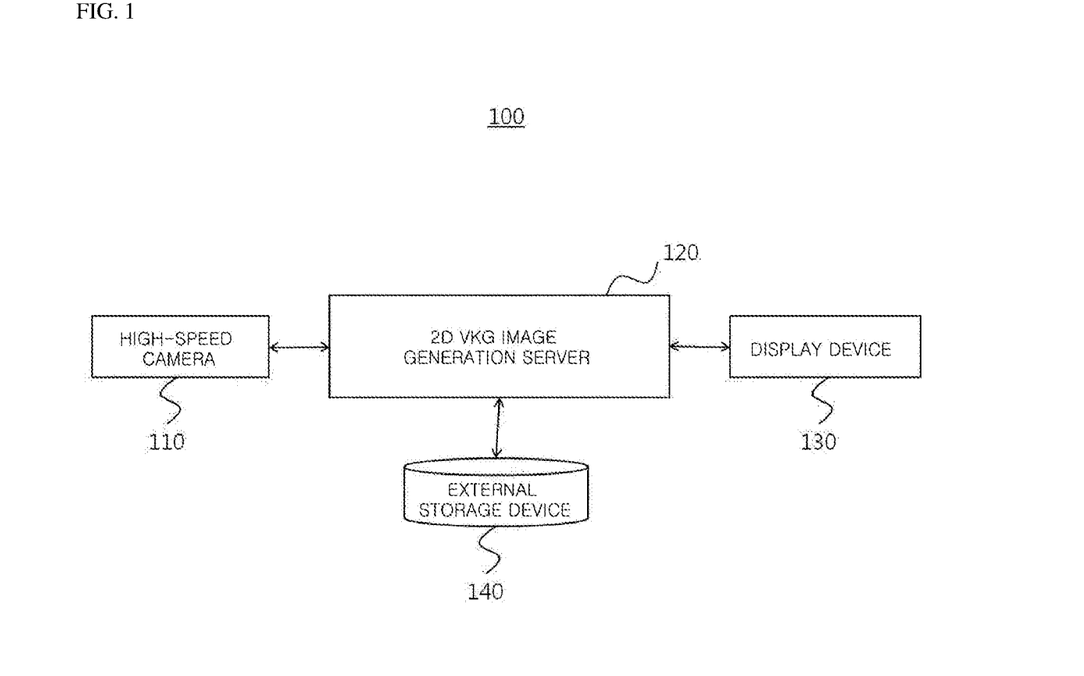
FIG. 1 is a block diagram of a two-dimensional scanning videokymography (2D VKG) image generation system according to an exemplary embodiment of the present invention.

FIG. 1 is a block diagram of a two-dimensional scanning videokymography (2D VKG) image generation system according to an exemplary embodiment of the present invention.

Referring to FIG. 1, a 2D VKG image generation system 100 includes an ultra-high speed camera 110, a 2D VKG image generation server 120, and a display device 130, and may further include an external storage device 140.

The ultra-high speed camera 110 may capture laryngeal endoscopy images and provide the captured laryngeal endoscopy images to the 2D VKG image generation server 120 or an image acquisition device which is not shown in the drawing but is provided outside or inside the 2D VKG image generation server 120.

The 2D VKG image generation server 120 is a device which may be connected to the ultra-high speed camera 110, the display device 130, or the external storage device 140 to perform a 2D VKG image generation method. Preferably, the 2D VKG image generation server 120 may generate 2D VKG images using laryngeal endoscopy images provided by the ultra-high speed camera 110 or ultra-high speed laryngeal endoscopy images pre-stored in the external storage device 140 or an internal storage device provided in the 2D VKG image generation server 120, and output the generated 2D VKG images to the display device 130.

The display device 130 is a device which may visually output the 2D VKG images generated by the 2D VKG image generation server 120 and the ultra-high speed laryngeal endoscopy images, and the external storage device 140 is a device which is separately provided outside the 2D VKG image generation server 120 and may store and manage the 2D VKG images generated by the 2D VKG image generation server 120 or the ultra-high speed laryngeal endoscopy images captured by the ultra-high speed camera 110.

Figure 2:
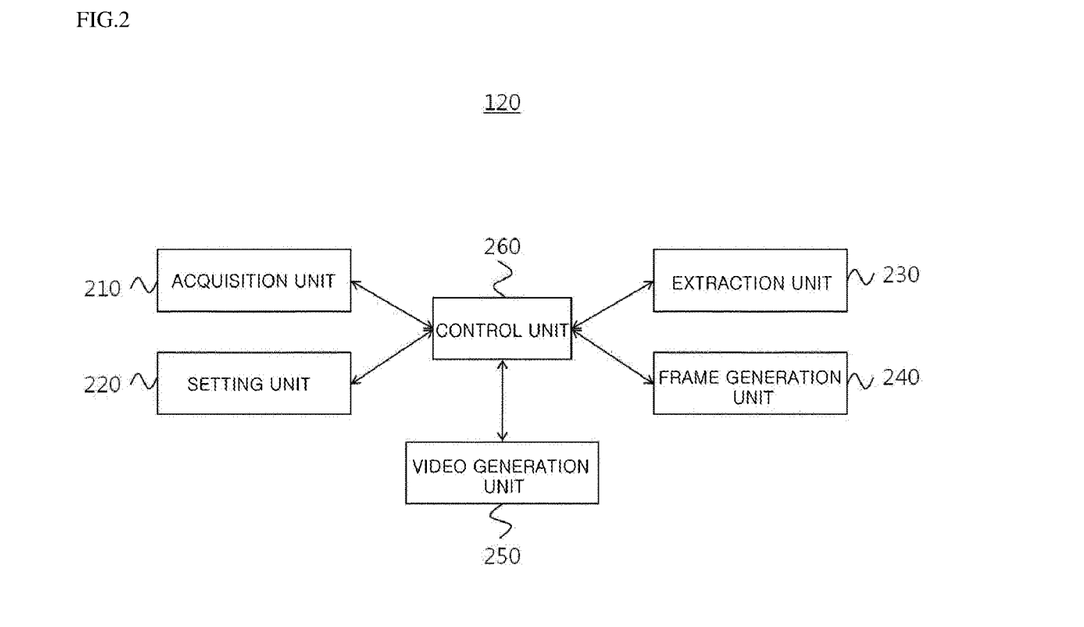
FIG. 2 is a block diagram of a 2D VKG image generation server of FIG. 1.

FIG. 2 is a block diagram of the 2D VKG image generation server of FIG. 1.

Referring to FIG. 2, the 2D VKG image generation server 120 includes an acquisition unit 210, a setting unit 220, an extraction unit 230, a frame generation unit 240, a video generation unit 250, and a control unit 260. Description will be made below with reference to FIGS. 4 to 6.

The acquisition unit 210 acquires monochromatic or color ultra-high speed laryngeal endoscopy images. Preferably, the acquisition unit 210 may receive ultra-high speed laryngeal endoscopy images in real time from the ultra-high speed camera 110 connected to the 2D VKG image generation server 120. More specifically, the acquisition unit 210 may convert the ultra-high speed laryngeal endoscopy analog images, which are captured in real time by the ultra-high speed camera 110, into ultra-high speed laryngeal endoscopy digital image data through an image acquisition device, such as a video capture board or the like, provided inside or outside the 2D VKG image generation server 120 and acquire the ultra-high speed laryngeal endoscopy digital image data in real time.

Also, the acquisition unit 210 may load ultra-high speed laryngeal endoscopy images pre-stored in the internal storage device of the 2D VKG image generation server 120 or the external storage device 140.

Here, the ultra-high speed laryngeal endoscopy images acquired through the acquisition unit 210 may be monochromatic or color images, which may improve discrimination for evaluation of pieces of anatomy, such as blood vessels, a tumor, and the like of vocal folds.

The setting unit 220 sets a target region and a pixel unit for generating 2D VKG images from the ultra-high speed laryngeal endoscopy images. Here, the target region is a region of the ultra-high speed laryngeal endoscopy images from which 2D VKG images will be generated, and the pixel unit corresponds to a predetermined number of pixel line of the target region or at least one of pixel constituting a pixel line, and is a basis for extracting pixel information from each frame of the ultra-high speed laryngeal endoscopy images.

Also, the setting unit 220 may set format information, for example, a frame rate and the like, of 2D VKG images to be generated.

Figure 4:
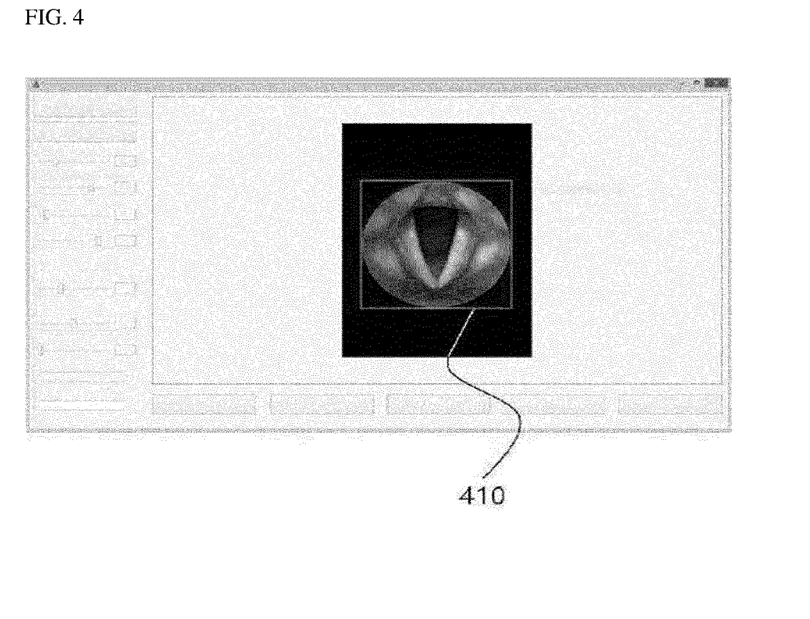
FIG. 4 is an example of a method of setting a target region for generating 2D VKG images.

For example, referring to FIG. 4, an ultra-high speed laryngeal endoscopy image acquired through the acquisition unit 210 is mostly black at an outer part thereof. Since there is a region unrelated to image information of vocal folds and a region excluding the vocal folds does not vibrate during an endoscopic examination, it is possible to exclude an unnecessary region through a bounding box 410 of FIG. 4 and set a target region from which 2D VKG images will be generated. Also, by setting the target region, it is possible to reduce a data storage space when generating 2D VKG images and increase an image processing rate.

The extraction unit 230 extracts pixel information of each frame of the ultra-high speed laryngeal endoscopy images according to the pixel unit in the target region. Preferably, the extraction unit 230 may extract as much pixel information as the pixel unit set by the setting unit 220 from each of the frames beginning with a first frame of the ultra-high speed laryngeal endoscopy images.

Also, the extraction unit 230 may extract pixel information of a specific frame among the ultra-high speed laryngeal endoscopy images and then determine a position next to a position from which the pixel information is extracted as a pixel information extraction position from which pixel information will be extracted in a frame next to the specific frame. In other words, the pixel information extraction position is determined to be a position next to a pixel position extracted from a previous frame, and is determined to move from left to right, from right to left, from top to bottom, or from bottom to top to move in a predetermined direction in all of the frames.

Figure 5:
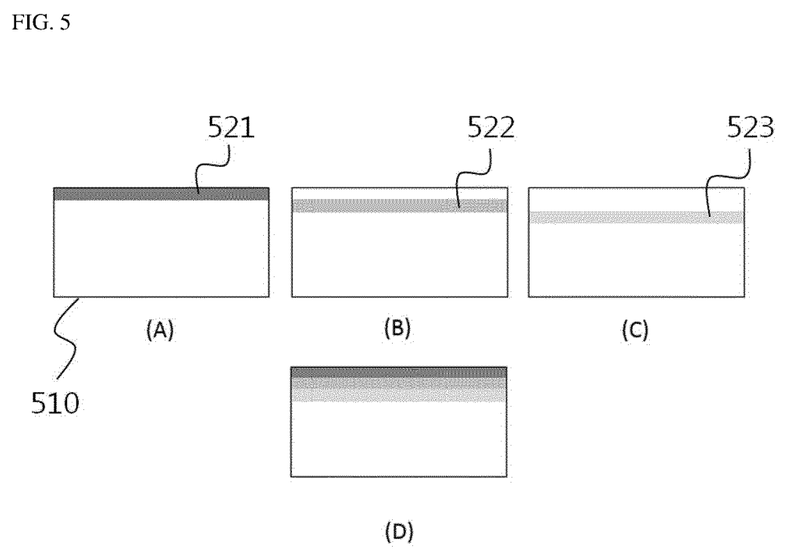
FIG. 5 is an example of a method of extracting pixel information of each frame and a method of combining extracted pixel information when a pixel unit is a pixel line.

As an example, referring to FIG. 5, when the setting unit 220 sets a target region 510, sets one pixel line as a pixel unit, and sets movement of the pixel information extraction position to be from top to bottom, the extraction unit 230 may extract first pixel information 521 from the target region 510 of a first frame, as shown in (A), move the pixel information extraction position to a location next to the location from which the first pixel information 521 is extracted, that is, in a downward direction, in a second frame to extract second pixel information 522, as shown in (B), move the pixel information extraction position in the downward direction from the location from which the second pixel information 522 is extracted in a third frame to extract third pixel information 523, as shown in (C), and extract pixel information of pixel lines from all subsequent frames in the same way.

Figure 6:
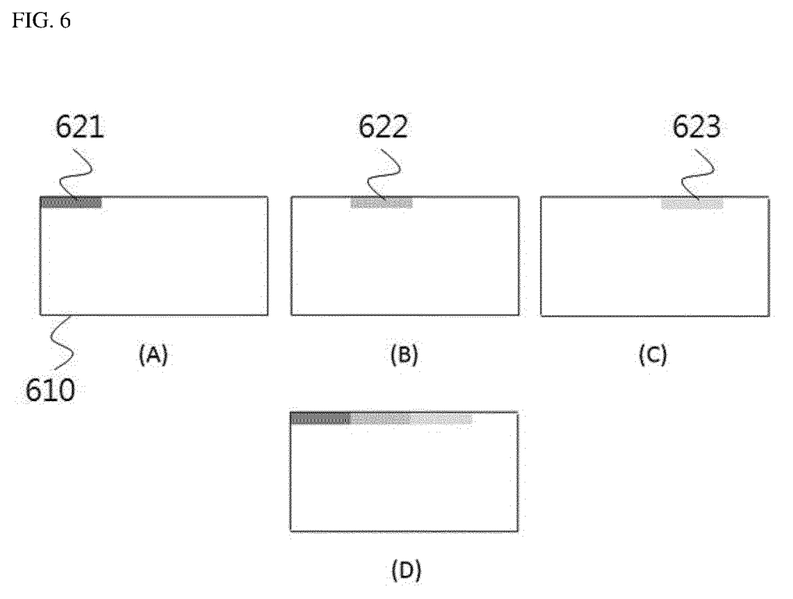
FIG. 6 is an example of a method of extracting pixel information of each frame and a method of combining extracted pixel information when a pixel unit is a predetermined number of pixel.

As another example, referring to FIG. 6, when the setting unit 220 sets a target region 610, sets a predetermined number of pixel as a pixel unit, and sets movement of the pixel information extraction position to be from left to right, the extraction unit 230 may extract first pixel information 621 from the target region 610 of a first frame, as shown in (A), move the pixel information extraction position to a location next to the location from which the first pixel information 621 is extracted, that is, in a rightward direction, in a second frame to extract second pixel information 622, as shown in (B), move the pixel information extraction position in the rightward direction from the location from which the second pixel information 622 is extracted in a third frame to extract third pixel information 623, as shown in (C), and extract pixel information of the predetermined number of pixel from all subsequent frames in the same way.

The frame generation unit 240 generates frames of 2D VKG images by combining the extracted pixel information of each of the frames. More specifically, the frame generation unit 240 may set the pixel information of each of the extracted frames of the ultra-high speed laryngeal endoscopy images as pixel information of a corresponding pixel position of a frame of 2D VKG images according to a pixel information extraction position from which the pixel information is extracted.

As an example, referring to FIG. 5, it is possible to generate a frame of 2D VKG images by combining the first pixel information 521 to the third pixel information 523 extracted from the first to third frames, as shown in (D). More specifically, in the frame of 2D VKG images, the first pixel information is set at a position corresponding to the pixel extraction position of the first pixel information 521, the second pixel information is set at a position corresponding to the pixel extraction position of the second pixel information, and the third pixel information is set at a position corresponding to the pixel extraction position of the third pixel information. In this way, each frame constituting 2D VKG images may be generated.

As another example, referring to FIG. 6, it is possible to generate a frame of 2D VKG images by combining the first pixel information 621 to the third pixel information 631 extracted from the first to third frames, as shown in (D). More specifically, in the frame of 2D VKG images, the first pixel information is set at a position corresponding to the pixel extraction position of the first pixel information 621, the second pixel information is set at a position corresponding to the pixel extraction position of the second pixel information, and the third pixel information is set at a position corresponding to the pixel extraction position of the third pixel information. In this way, each frame constituting 2D VKG images may be generated.

Preferably, when the extraction unit 230 extracts a last predetermined number of pixel line or a last predetermined number of pixel from a frame of an ultra-high speed laryngeal endoscopy image and the frame generation unit 240 generates one frame of 2D VKG images, the extraction unit 230 may perform the pixel information extraction process in the same way beginning with an initial position, that is, a position corresponding to a position in a first frame from which pixel information is extracted, in the next frame of 2D VKG images, and the frame generation unit 240 may generate frames of 2D VKG images on the basis of the extracted pixel information in the same way as that described above. In other words, a pixel information extraction process may be performed on all frames of the ultra-high speed laryngeal endoscopy images to generate frames of 2D VKG images.

In one embodiment, the frame generation unit 240 may correct brightness, saturation, blurring, sharpness, or rotation of the generated 2D VKG images. More specifically, when the number of predetermined pixel lines or predetermined pixels is large, the generation of the frames of 2D VKG images by combining the pixel information may cause a drastic color change at a boundary between combined pixel lines or pixels. Therefore, to correct the drastic color change at the boundary between combined pixel information, image processing, such as brightness, saturation, blurring, sharpness, rotation, and the like, of each of the frames may be performed.

The video generation unit 250 generates a 2D VKG video by combining the frames of 2D VKG images generated by the frame generation unit 240.

Also, the video generation unit 250 may store or output the generated 2D VKG video to the display device 130 connected to the 2D VKG image generation server 120.

More specifically, the generated 2D VKG video may be stored in the internal storage device provided in the 2D VKG image generation server 120 or the external storage device 140.

The control unit 260 controls data flow and operation of the acquisition unit 210, the setting unit 220, the extraction unit 230, the frame generation unit 240, and the video generation unit 250.

Figure 3:
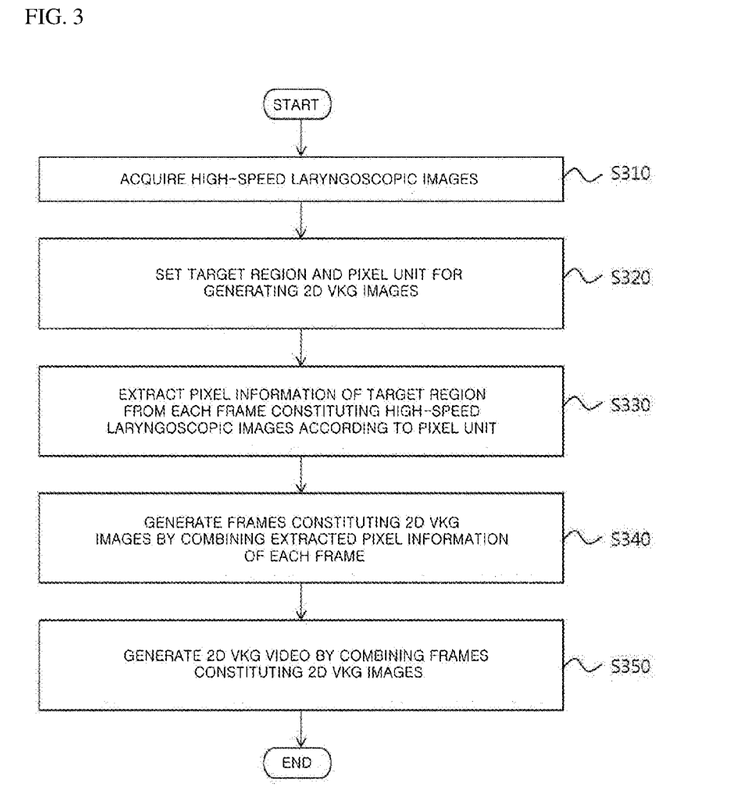
FIG. 3 is a flowchart of a 2D VKG image generation method performed in the 2D VKG image generation system of FIG. 1.

FIG. 3 is a flowchart of a 2D VKG image generation method performed in the 2D VKG image generation system of FIG. 1. Description will be made below with reference to FIGS. 7 to 12.

The acquisition unit 210 acquires ultra-high speed laryngeal endoscopy images (step S310). Preferably, the acquisition unit 210 may acquire the ultra-high speed laryngeal endoscopy images by receiving ultra-high speed laryngeal endoscopy images captured by the ultra-high speed camera 110 in real time or loading pre-stored ultra-high speed laryngeal endoscopy images.

The setting unit 220 sets a target region and a pixel unit for generating 2D VKG images (step S320). In other words, the setting unit 220 sets the target region, which is a region of the ultra-high speed laryngeal endoscopy images from which 2D VKG images will be generated, and sets a unit of pixels in which pixels will be extracted from each frame constituting the ultra-high speed laryngeal endoscopy images.

The extraction unit 230 extracts pixel information of each frame constituting the ultra-high speed laryngeal endoscopy images according to the pixel unit in the target region (step S330). More specifically, the extraction unit 230 sequentially extracts the pixel information of the pixel unit from each of all of the frames constituting the ultra-high speed laryngeal endoscopy images.

The frame generation unit 240 generates frames of 2D VKG images by combining the extracted pixel information of each frame (step S340). Preferably, the extraction unit 230 may extract the pixel information from all of the frames of the ultra-high speed laryngeal endoscopy images acquired through the acquisition unit 210, and the frame generation unit 240 may generate frames which will constitute the 2D VKG images by combining the extracted pixel information.

Figure 7:
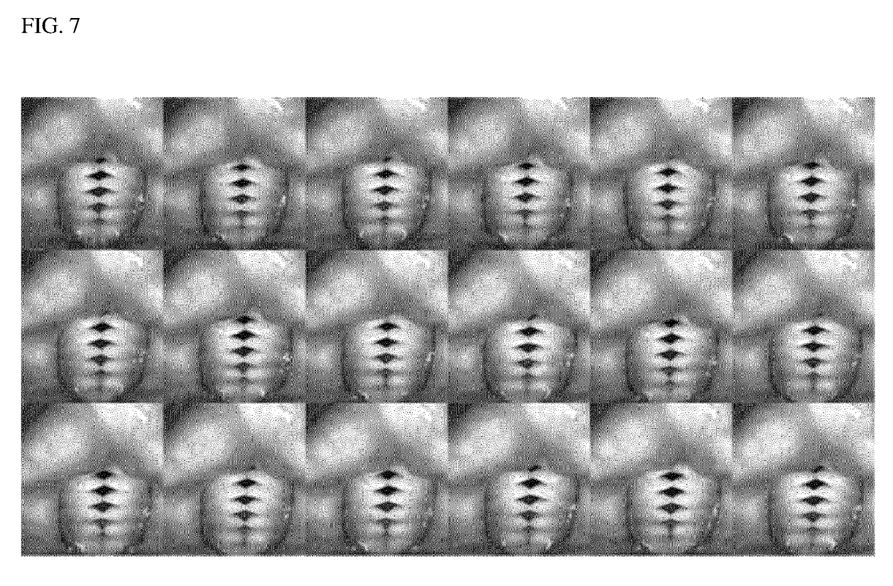
FIG. 7 is an example of a change of 2D VKG images generated when a pixel unit is one pixel line.
Figure 8:
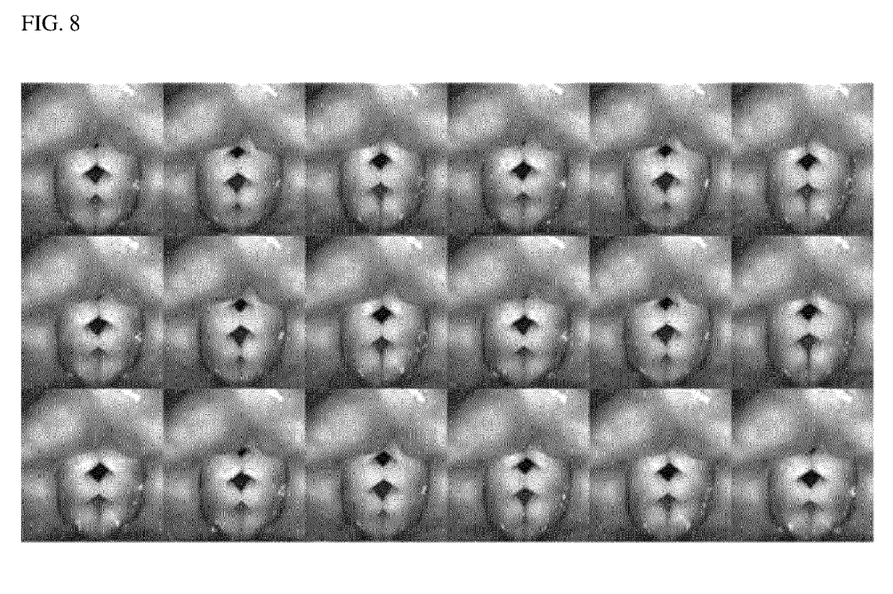
FIG. 8 is an example of a change of 2D VKG images generated when a pixel unit is two pixel lines.
Figure 9:
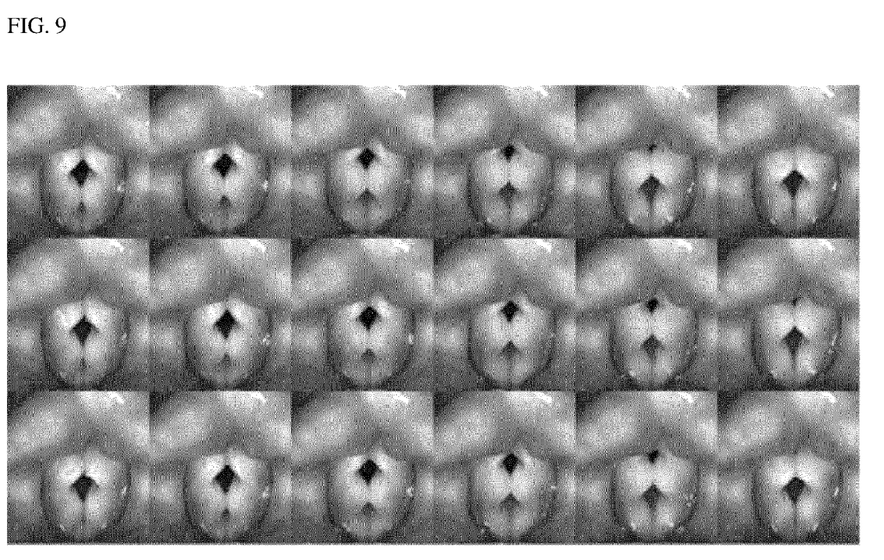
FIG. 9 is an example of a change of 2D VKG images generated when a pixel unit is three pixel lines.
Figure 10:
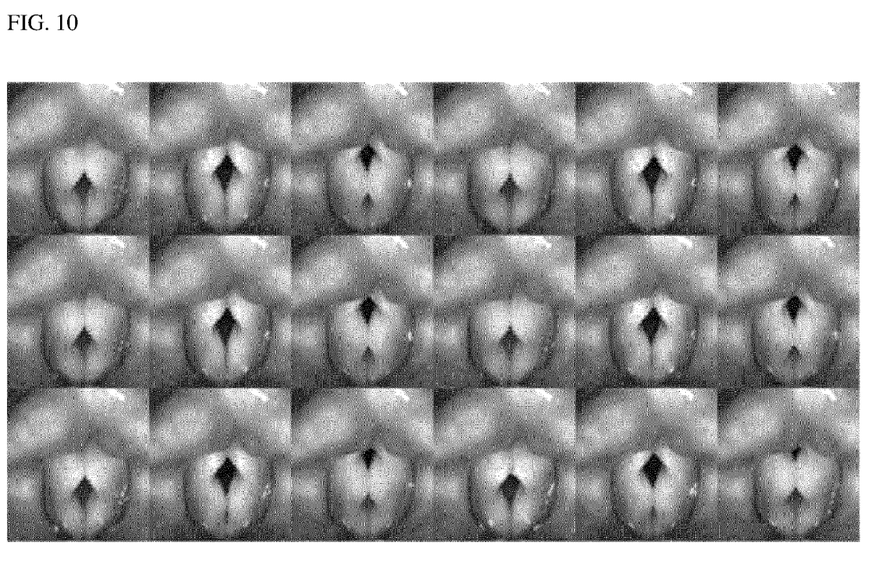
FIG. 10 is an example of a change of 2D VKG images generated when a pixel unit is four pixel lines.

The video generation unit 250 generates a 2D VKG video by combining the frames of 2D VKG images (step S350). For example, the video generation unit 250 may generate the 2D VKG video by combining frames generated using one pixel line as the pixel unit, as shown in FIG. 7, generate the 2D VKG video by combining frames generated using two pixel lines as the pixel unit, as shown in FIG. 8, generate the 2D VKG video by combining frames generated using three pixel lines as the pixel unit, as shown in FIG. 9, and generate the 2D VKG video by combining frames generated using four pixel lines as the pixel unit, as shown in FIG. 10.

Figure 11:
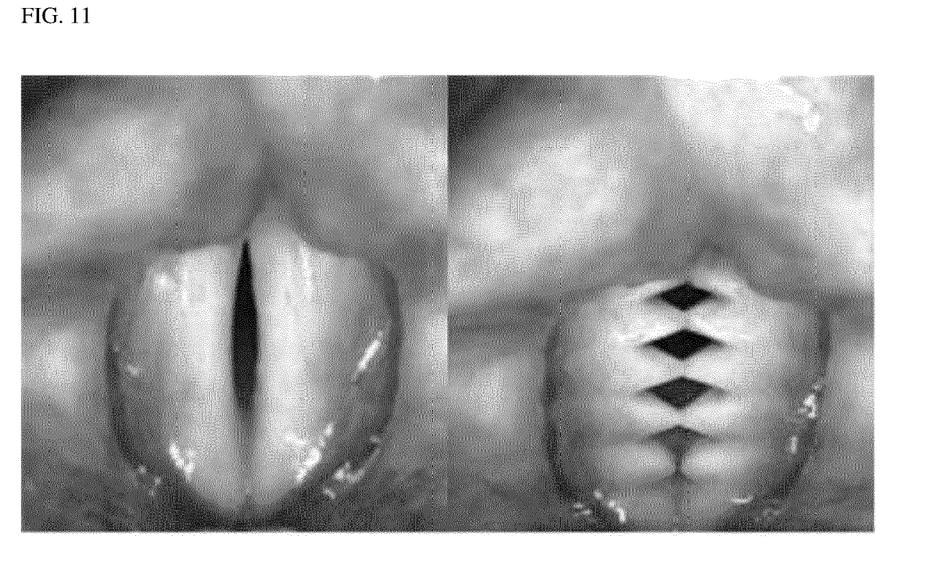
FIG. 11 is an example in which an ultra-high speed laryngeal endoscopy image and a generated 2D VKG image are output.
Figure 12:
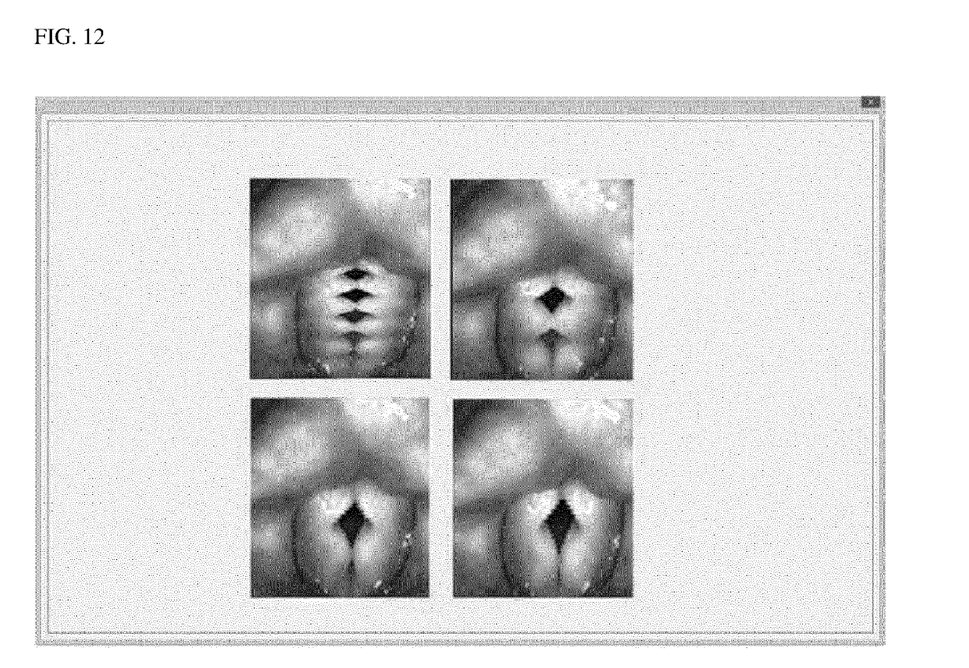
FIG. 12 is an example in which a plurality of generated 2D VKG images are simultaneously output on one screen.

Also, the video generation unit 250 may store or output the generated video through the display device 130. For example, the video generation unit 250 may simultaneously output an ultra-high speed laryngeal endoscopy image and a 2D VKG image generated using the ultra-high speed laryngeal endoscopy image on the display device 130, as shown in FIG. 11, to facilitate a comparison of the two images, and may simultaneously output individual 2D VKG images which are generated using one pixel line, two pixel lines, three pixel lines, and four pixel lines as a pixel unit on the display device 130 for a comparison as shown in FIG. 12.

Meanwhile, the 2D VKG generation method according to an exemplary embodiment of the present invention can be implemented as a computer-readable code in a computer-readable recording medium. The computer-readable recording medium includes all types of recording devices in which data that can be read by a computer system is stored.

Examples of the computer-readable recording medium are a read-only memory (ROM), a random access memory (RAM), a compact disc ROM (CD-ROM), a magnetic tape, a hard disk, a floppy disk, a mobile storage device, a non-volatile memory (flash memory), an optical data storage device, and the like.

Also, the computer-readable recording medium may be distributed to computer systems that are connected via a computer network and may be stored and executed as a code readable in a distributed manner.

Although exemplary embodiments of a method of generating 2D VKG images using real-time or pre-stored ultra-high speed laryngeal endoscopy images, a 2D VKG generation server for performing the method, and a recording medium storing the method according to the present invention have been described above, the present invention is not limited thereto. The present invention can be varied in various ways within the scope of the claims, the detailed description thereof, and the appended drawings, and the variations still fall within the present invention.

The invention claimed is:

1. A method of generating two-dimensional scanning videokymography (2D VKG) images using real-time or pre-stored ultra-high speed laryngeal endoscopy images in a 2D VKG image generation server, the method comprising:
   (a) acquiring monochromatic or color ultra-high speed laryngeal endoscopy images of an entire laryngeal region;
   (b) setting a target region through a bounding box which excludes black at an outer part of the ultra-high speed laryngeal endoscopy images and a pixel unit a predetermined number of pixel lines of the target region and movement of a pixel information extraction position to be from top to bottom for generating 2D VKG images from the ultra-high speed laryngeal endoscopy images;
   (c) extracting pixel information of each frame of the ultra-high speed laryngeal endoscopy images according to the predetermined number of pixel lines in the target region;
   (d) generating frames of 2D VKG images by combining the extracted pixel information of each frame; and
   (e) generating a 2D VKG video by combining the frames of the 2D VKG images,
   wherein step (c) comprises extracting pixel information of a specific frame among frames of the ultra-high speed laryngeal endoscopy images and then determining a next pixel information extraction position to be below the pixel information extraction position from a previous frame such that the 2D VKG images are constructed by extracting and combining one to four horizontal pixel lines from top to bottom with the image,
   wherein step (d) comprises setting the extracted pixel information of each frame as pixel information of a corresponding position in a frame of the 2D VKG images according to an extraction position of the extracted pixel information, and
   wherein each frame of step (c) is generated when a last predetermined number of pixel lines from a frame of the ultra-high speed laryngeal endoscopy image is extracted.

2. The method of claim 1, wherein step (a) comprises receiving the ultra-high speed laryngeal endoscopy images in real time from an ultra-high speed camera connected to the 2D VKG image generation server or loading ultra-high speed laryngeal endoscopy images pre-stored in the 2D VKG image generation server.

3. The method of claim 1, wherein step (d) further comprises correcting brightness, saturation, blurring, sharpness, or rotation of the frames of the generated 2D VKG images.

4. The method of claim 1, wherein step (e) further comprises storing the 2D VKG video or outputting the 2D VKG video to a display device connected to the 2D VKG image generation server.

5. A server for generating two-dimensional scanning videokymography (2D VKG) images, the server is implemented at least by a hardware including a processor and is configured:
- to acquire monochromatic or color ultra-high speed laryngeal endoscopy images of an entire laryngeal region;
- to set a target region through a bounding box which excludes black at an outer part of the ultra-high speed laryngeal endoscopy images and a predetermined number of pixel lines of the target region and movement of a pixel information extraction position to be from top to bottom for generating 2D VKG images from the ultra-high speed laryngeal endoscopy images;
- to extract pixel information of each frame of the ultra-high speed laryngeal endoscopy images according to the predetermined number of pixel lines in the target region;
- to generate frames of 2D VKG images by combining the extracted pixel information of each frame; and
- to generate a 2D VKG video by combining the frames of the 2D VKG images, wherein the server is configured to extract pixel information of a specific frame among frames of the ultra-high speed laryngeal endoscopy images and then determine a next pixel information extraction position to be below the pixel information extraction position from a previous frame a next pixel information extraction position to be below such that the 2D VKG images are constructed by extracting and combining one to four horizontal pixel lines from top to bottom with the image, wherein step (d) comprises setting the extracted pixel information of each frame as pixel information of a corresponding position in a frame of the 2D VKG images according to an extraction position of the extracted pixel information, and wherein each frame of step (c) is generated when a last predetermined number of pixel lines from a frame of the ultra-high speed laryngeal endoscopy image is extracted.

6. The server of claim 5, wherein the server is configured to receive the ultra-high speed laryngeal endoscopy images in real time from an ultra-high speed camera connected to the server for generating 2D VKG images or load ultra-high speed laryngeal endoscopy images pre-stored in the server for generating 2D VKG images.

7. The server of claim 5, wherein the server is configured to correct brightness, saturation, blurring, sharpness, or rotation of the frames of the generated 2D VKG images.

8. The server of claim 5, wherein the server is configured to store the 2D VKG video or output the 2D VKG video to a display device connected to the server for generating 2D VKG images.

* * * * *